(12) United States Patent
Dewey (10) Patent No.: US 7,588,553 B2
(45) Date of Patent: Sep. 15, 2009

(54) PHACOEMULSIFICATION DEVICE HAVING ROUNDED EDGES

(76) Inventor: Steven H. Dewey, 209 S. Nevada Ave., Colorado Springs, CO (US) 80903

( * ) Notice: Subject to any disclaimer, the term of this patent is extended or adjusted under 35 U.S.C. 154(b) by 0 days.

(21) Appl. No.: 11/221,178

(22) Filed: Sep. 6, 2005

(65) Prior Publication Data

US 2006/0052758 A1 Mar. 9, 2006

Related U.S. Application Data

(60) Provisional application No. 60/607,867, filed on Sep. 7, 2004.

(51) Int. Cl.
*A61B 17/20* (2006.01)
(52) U.S. Cl. .......................... 604/22; 606/107
(58) Field of Classification Search ................. 604/272, 604/28, 22; 60/28; 606/167, 168, 171
See application file for complete search history.

(56) References Cited

U.S. PATENT DOCUMENTS

| | | | |
|---|---|---|---|
| 4,959,049 A | | 9/1990 | Smirmaul |
| 5,213,569 A | * | 5/1993 | Davis ........................... 604/22 |
| 5,676,649 A | * | 10/1997 | Boukhny et al. .............. 604/22 |
| 5,718,676 A | * | 2/1998 | Barrett ......................... 604/22 |
| 5,788,679 A | | 8/1998 | Gravlee, Jr. |
| 5,830,192 A | * | 11/1998 | Van Voorhis ................ 604/533 |
| 5,980,529 A | * | 11/1999 | Strukel ......................... 604/22 |
| 5,993,408 A | | 11/1999 | Zaleski |
| 5,993,409 A | * | 11/1999 | Maaskamp ................... 604/22 |
| 6,007,555 A | | 12/1999 | Devine |
| 6,126,629 A | | 10/2000 | Perkins |
| 6,159,175 A | | 12/2000 | Strukel et al. |

(Continued)

FOREIGN PATENT DOCUMENTS

SU 850084 B * 7/1981

OTHER PUBLICATIONS

Davis, Peter L., "Phaco Transducers: Basic Principles and Corneal Thermal Injury," Eur. J. Implant Ref. Surg., vol. 5, pp. 109-112, Jun. 1993.
Davis, Peter L., "Cavitating Microbubbles Create Shock Waves that Emulsify Cataract," The Art of Phacoemulsification, Chpt. 4, Jaypee Bros., New Delhi, 2001.

(Continued)

*Primary Examiner*—Nicholas D Lucchesi
*Assistant Examiner*—Laura A Bouchelle
(74) *Attorney, Agent, or Firm*—Jeffrey L. Thompson; Thompson & Thompson, P.A.

(57) ABSTRACT

A phacoemulsification needle is disclosed having a hollow member with an inner surface, an outer surface, and a distal end tip. The distal end tip has an outer edge portion and an inner edge portion both of which are rounded to eliminate any sharp edges. The needle can be used to deliver ultrasonic energy to a surgical site, such as a cataract, to emulsify unwanted tissue and to aspirate the tissue through the lumen of the hollow member without using any sharp surfaces for cutting. The rounded outer and inner edge portions of the distal end tip of the needle increase the safety of the surgical procedure by reducing the risk of damage to the capsule or other intraocular structures or tissues near the surgical site. This improvement in safety has allowed the development of new needle configurations to improve the efficiency of phacoemulsification, several of which are disclosed herein.

24 Claims, 7 Drawing Sheets

U.S. PATENT DOCUMENTS

| | | | | |
|---|---|---|---|---|
| 6,283,974 B1 * | 9/2001 | Alexander | ................. | 606/107 |
| 6,533,750 B2 | 3/2003 | Sutton et al. | | |
| 7,204,820 B2 * | 4/2007 | Akahoshi | ..................... | 604/22 |
| 2001/0031951 A1 * | 10/2001 | Pezzola | ...................... | 604/275 |
| 2004/0204690 A1 * | 10/2004 | Yashiro et al. | .............. | 604/257 |

OTHER PUBLICATIONS

McNeill, James I., "Flared Phacoemulsification Tips to Decrease Ultrasound Time and Energy in Cataract Surgery," J. Cataract Regract. Surg., vol. 27, Sep. 2001.

Davis, Peter L., Declaration dated May 18, 2006.

* cited by examiner

PHACOEMULSIFICATION DEVICE HAVING ROUNDED EDGES

RELATED APPLICATIONS

This application claims priority of U.S. Provisional Application No. 60/607,867 filed on Sep. 7, 2004, the content of which is incorporated herein by reference.

BACKGROUND OF THE INVENTION

1. Field of the Invention

The present invention relates generally to surgical instruments. In particular, the present invention relates to improved phacoemulsification needles used in ophthalmic surgery.

2. Description of the Related Art

Phacoemulsification needles are used for breaking apart and removing unwanted tissue and material, particularly cataracts. It should be understood that phacoemulsification procedures can also be used to remove the soft lens of an eye before the soft lens becomes a cataract, and that the procedures described herein for removing cataracts also encompasses such soft lens removal and other common procedures utilizing phacoemulsification. A phacoemulsification needle is typically attached to a handpiece that vibrates the needle at an ultrasonic frequency during a surgical procedure. The phacoemulsification procedure involves using the vibrating needle to ultrasonically fragment a cataract while simultaneously introducing fluid into the eye and withdrawing the fluid and the fragmented cataract particles through the hollow needle. The cataract is emulsified by the distal end tip of the needle and removed from the eye through the hollow needle. A suction source attached to the handpiece is used to supply the necessary suction to the needle.

Current phacoemulsification needles remove nuclear material by use of ultrasound energy, the effect of which forms a combination of cutting and cavitation to fragment the lens. A sharp edge is used to enhance the cutting effect, and this effect is further enhanced by aspiration and vacuum. The needle at the end of the handpiece is hollow, and the edge is typically defined by having a surface with edges that conform to an acute angle (less than 90 degrees) and come to a point. Slicing a hollow metal pipe at any angle will create the sharp edge described.

Fundamentally, the sharp edge of the phacoemulsification probe enhances the cutting ability of the needle, but it poses several dangers. The greatest danger is the ability of the cutting edge to tear intraocular structures while trying to remove the nuclear material. This may result in damage to the lens capsule and iris. Incidentally, the tip passing through the incision itself can cause damage to the incision.

Typically, the sharpened or honed edge is found on both the outer edge of the distal tip of the end of the needle and along the inner edge of the needle (i.e., the outer edge of the lumen). During phacoemulsification, aspiration of eye tissue is achieved by drawing fluid through the inner lumen of the hollow emulsification needle after it has been subjected to ultrasound energy. Even when vacuum is turned off, an imbalance of the flow of fluid to stabilize the anterior chamber of the eye (infusion) and/or the process of the application of ultrasonic energy can create a vacuum-like effect to draw eye structures into the lumen of the phacoemulsification needle with or without intent.

Phacoemulsification needles with sharp edges on any surface can cause damage to ocular tissue. Incidental contact of these sharp edges, either with the sharpened knife-like honing of the edge, or with burrs on the edge remaining from poor manufacturing techniques, will cause damage to the tissues these edges contact. Rounding the outer edge does prevent damage due to an incidental contact. This is analogous to sanding a piece of rough wood to prevent it from snagging on a fabric. Smoothing this outer surface thus prevents damage by either dulling the honed, sharpened surface, or by removing incidental burrs.

The iris is a readily distensible tissue that typically is not involved in intraocular surgery as the dilation is in most cases adequate to keep it out of the field of the active aspiration/emulsification occurring at the distal tip of the phacoemulsification needle. However, as more lens material is removed, the capsule becomes exposed to a greater degree. Likewise, it becomes much more distensible as it becomes more exposed. The anterior capsule is always exposed during phacoemulsification, to a greater degree than the distensible iris. The anterior capsule is perhaps the least distensible of the tissues described, but can be damaged as well.

Damage to the anterior and/or posterior capsule occurs in 2 to 5% of phacoemulsification surgeries, and can be identified as occurring during the use of the phacoemulsification needle in the majority of cases. Damage to the capsule during this stage of surgery significantly compromises the likelihood of successfully removing the cataract without loss of vitreous, and can be shown to compromise the result of the cataract surgery by significantly increasing the intraoperative and postoperative complication rates. The frequency of damage to the iris during cataract surgery is not documented, but can also result in significant compromise of the surgical result.

Techniques to keep distensible eye tissues away from the phacoemulsification needle rely on surgeon ability and instrumentation. Anterior chamber stability is achieved by balancing the inflow of infusion fluid with the removal of this fluid through aspiration. While the phacoemulsification device may be able to achieve this to a large degree, the surgeon-specific technique is the creation of appropriately sized incisions to prevent excess leakage. Such excess leakage can increase outflow and threaten chamber stability. Modifications to phacoemulsification needles have been created to avoid a sudden increase in fluid outflow, called "surge," which occurs when an absolute or partial occlusion of the phacoemulsification outflow system is suddenly released and outflow exceeds inflow. In addition, surgeon technique may not be sufficient to anticipate unwanted contact of these distensible tissues to the phacoemulsification tip. Situations such as poor iris dilation, an unstable anterior chamber, or surgeon technique can result in an increased likelihood of a distensible eye tissue coming in contact with any of the sharpened or burred edges of a phacoemulsification needle, and this contact is likely to create damage to those eye tissues.

Another problem with prior art phacoemulsification needles is that active aspiration of a distensible ocular tissue can cut or damage that tissue by rubbing it against the sharp internal edge of the distal tip (i.e., the far distal inner edge of the lumen) or against small burrs that may exist despite honing this inner edge surface. As previously discussed, these distensible tissues can be aspirated due to poor chamber stability (such as is seen when the incision sizes are not appropriate and allow excessive outflow), poor iris dilation, or poor surgeon technique as examples. Contact of these tissues with the inner edge of the tip of the phacoemulsification needle (i.e., the outer edge of the inner lumen of the needle) can result in severe damage to these tissues, either from direct cutting of the sharp surface or through ripping or sawing as caused by the roughened burrs.

One possible myth that has arisen from observing the breaking of the capsule after aspirating it into a phacoemulsification tip, or any other hollow intraocular instrument designed for aspiration, is that a "vacuum" break can occur. It is much more likely that the "vacuum" involved merely stabilizes the distensible capsule and allows it to be cut by either the sharpened, honed inner edge, or an incidental burr as a result of poor manufacturing.

A "knuckle" tip for a phacoemulsification needle was demonstrated by Dr. Akahoshi at the ASCRS meeting in April 2004 in San Diego, Calif. This tip resembled the fat end of a pear attached to the end of a phacoemulsification needle, with a central rounded aspirating port. However, the rim of the needle exceeded the standard rim thickness and diameter and was designed to avoid aspirating the capsule. This knuckle-tipped needle requires a new surgical technique to be used by cataract surgeons and a separate device to cut a cataract before removal, thereby reducing surgical efficiency.

Another phacoemulsification needle has been developed by Alcon of Fort Worth, Tex., which has an accessory aspiration port far away from the primary aspirating port at the distal end of the phacoemulsification needle. This port is called the "ABS" port, and is used to stabilize the anterior chamber during phacoemulsification when the primary aspirating tip is occluded. This tip has no role in the direct phacoemulsification of nuclear material, never comes in direct contact with intraocular structures, and is not rounded, dull, detuned or blunt.

There is a need in the industry for an improved phacoemulsification needle that minimizes the risk of damage to a patient's eye, while maintaining its effectiveness and efficiency for phacoemulsification procedures.

SUMMARY OF THE INVENTION

A phacoemulsification needle according to the present invention has a hollow member with an inner surface defining a lumen, an outer surface, and a distal end tip. The distal end tip has an outer edge portion and an inner edge portion, both of which are rounded to eliminate any sharp edges. The needle can be used to deliver ultrasonic energy to a surgical site, such as a cataract, to emulsify unwanted tissue and to aspirate the tissue through the lumen of the hollow member without using any sharp surfaces for cutting. The rounded outer and inner edge portions of the distal end tip of the needle increase the safety of the surgical procedure by reducing the risk of damage to the capsule and other intraocular structures or tissues at or near the surgical site. This improvement in safety has allowed the development of new needle configurations to improve the efficiency of phacoemulsification, several of which are disclosed herein.

According to a broad aspect of the present invention, a phacoemulsification needle is provided, comprising: a hollow member having an inner surface, an outer surface, and a distal end tip; wherein the distal end tip has an outer edge portion and an inner edge portion, and wherein the outer and inner edge portions are rounded to eliminate any sharp edges.

According to another broad aspect of the present invention, a method of performing phacoemulsification is provided, comprising the steps of: providing a phacoemulsification needle comprising a hollow member having an inner surface, an outer surface, and a distal end tip, the distal end tip having outer and inner edge portions which are rounded to eliminate any sharp edges; and using the phacoemulsification needle to deliver ultrasonic energy to emulsify unwanted tissue at a surgical site and to aspirate the unwanted tissue through the hollow member without using a sharp surface to cut the unwanted tissue.

According to another broad aspect of the present invention, a phacoemulsification instrument is provided, comprising: a source of ultrasonic energy; a plurality of ribs arranged in a pattern and extending from the source of ultrasonic energy, the ribs being operable to transmit ultrasonic forces for removing material in close proximity to respective distal tips of the ribs; and an outer sleeve positioned over and supporting the plurality of ribs.

Numerous other objects and features of the present invention will be apparent to those skilled in this art from the following description wherein there is shown and described exemplary embodiments of the present invention, simply by way of illustration of the modes best suited to carry out the invention. As will be realized, the invention is capable of other different embodiments, and its several details are capable of modification in various obvious aspects without departing from the invention. Accordingly, the drawings and description should be regarded as illustrative in nature and not restrictive.

BRIEF DESCRIPTION OF THE DRAWINGS

The present invention will become more clearly appreciated as the disclosure of the invention is made with reference to the accompanying drawings. In the drawings.

DETAILED DESCRIPTION OF THE INVENTION

Several embodiments of phacoemulsification needles and device according to the present invention will now be described with reference to FIGS. 1 to 45 of the accompanying drawings.

A phacoemulsification needle 10 according to a first embodiment of the present invention is shown in FIGS. 1 to 5. The needle 10 includes a hollow member 11 having an inner surface 12, a cylindrical outer surface 13, and a distal end tip 14. The distal end tip 14 has a rounded outer edge 15 and a rounded inner edge 16 and is carefully manufactured to avoid or eliminate any surfaces coming to a sharp point or sharp edge. Accordingly, the distal end tip 14 of the hollow needle 10 displays no surface coming to a sharp point or sharp edge.

Figure 1:
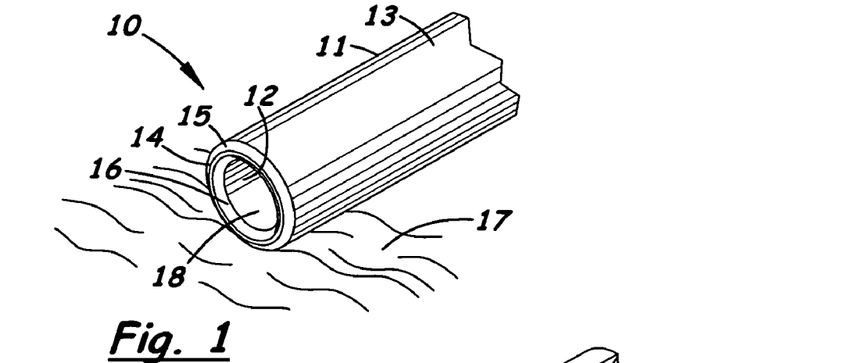
FIG. 1 is a perspective view of a phacoemulsification needle having an outer edge touching a capsule of an eye without aspiration.

The lens capsule 17, in its flaccid or resting state empty of contents, is essentially flat, depending on the fluidics in the eye at the time of observation. Typically it lies like a tablecloth draped over a bucket, provided the fluidics are at neutral. It is not under significant tension under most circumstances once the contents have been removed. In this configuration, as illustrated in FIG. 1, only the portion of the rounded outer edge 15 of the distal tip 14 of the needle 10 is in contact with the capsule 17 when the needle 10 is touched to the capsule 17 as one would touch a vacuum-cleaner nozzle to a table cloth without the vacuum cleaner being on.

Figure 2:
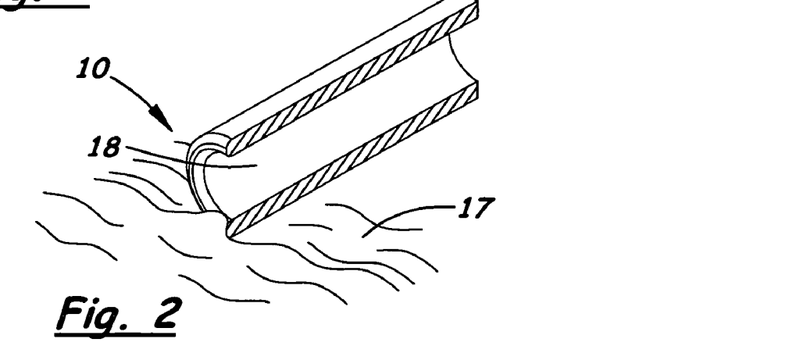
FIG. 2 is a cutaway perspective view of the phacoemulsification needle of FIG. 1 when aspiration is used to draw eye tissue into the end of the needle.
Figures 3, 4:
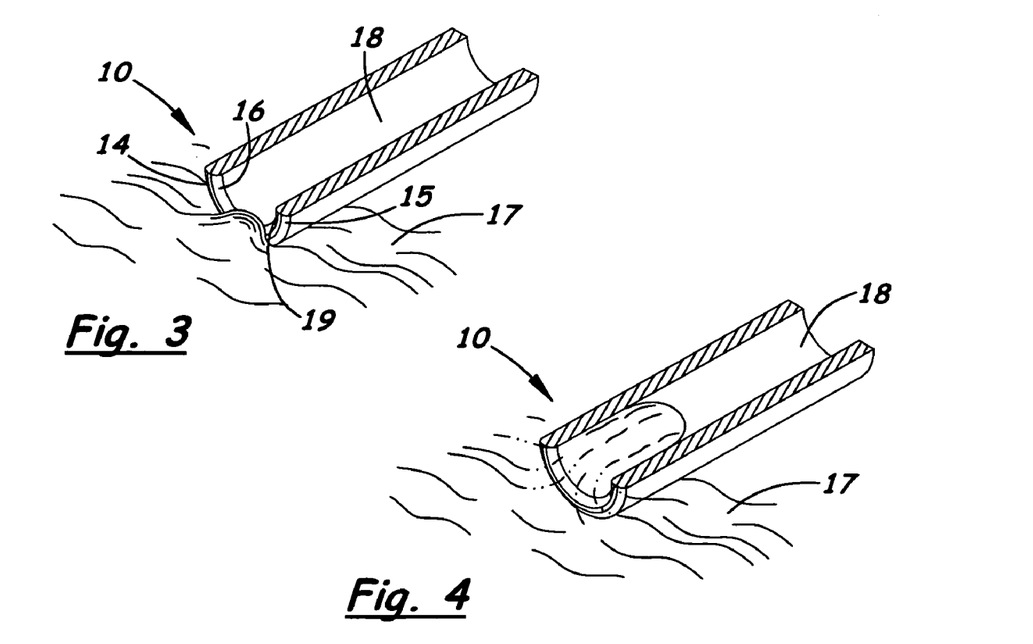
FIG. 3 is another cutaway perspective view of the needle of FIG. 2 showing the rounded inner and outer edges of the needle with the eye tissue partly aspirated into contact therewith according to the present invention.
FIG. 4 is a cutaway perspective view of the needle shown in FIGS. 1 to 3 during an aspirating procedure in which eye tissue is fully occluded within the needle.
Figure 5:
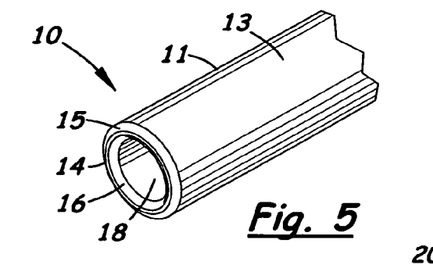
FIG. 5 is a perspective view of a needle having a straight tip configuration with rounded inner and outer edges according to one embodiment of the present invention.

With aspiration, as shown in FIGS. 2 to 4, the capsule 17 starts to be drawn into the lumen 18 of the needle 10, as shown in FIGS. 2 and 3. With increasing aspiration, the capsule 17 can fully occlude the needle 10, as shown in FIG. 4, so that the capsule 17 contacts substantially the entire inner edge 16 of the distal tip 14, much as a tablecloth would be drawn into a vacuum cleaner nozzle when the vacuum is turned on. In this case, the capsule 17 is drawn around the rounded outer edge 15, the distal face 19, the rounded inner edge 16, and into the lumen 18 of the needle 10.

The rounded inner edge 16 of the phacoemulsification needle 10 according to the present invention comes into contact with the capsule 17 only during aspiration (or with an imbalance of the normal flow of infusion out of the anterior chamber through the hollow needle), as depicted in FIGS. 2 to 4. The inner edge 16 can be distinguished from the outer edge 15 region of the needle 10 that passively contacts the capsule 17 without aspiration present, as depicted in FIG. 1. Both the inner edge 16 and outer edge 15 of the distal tip 14 of the needle 10 are rounded to eliminate any sharp edges so that the integrity of the capsule 17 and other intraocular structures that are aspirated into the lumen 18 of the needle 10 can be maintained.

Figures 7, 8:
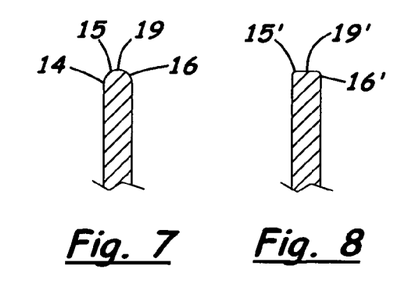
FIG. 7 is a cross section view of a rounded edge for a phacoemulsification needle according to the present invention.
FIG. 8 is a cross section view of another form of rounded edge for a phacoemulsification needle according to the present invention.

Example cross sections of the rounded surfaces 15, 16, 19 at the distal end 14 of the needle 10 are shown in FIGS. 7 and 8. In FIG. 7 a cross section of a distal end having a filly rounded edge is shown, while in FIG. 8 a cross section of a distal end with a blunt distal face 19' and rounded outer and inner edges 15', 16' is shown. In both cases, all sharp edges are eliminated at the distal end. Rounded surfaces on the outer and inner edges 15, 16 (FIG. 7) or 15', 16' (FIG. 8) of the distal tip 14 of the phacoemulsification needle 10 according to the present invention are those surfaces that are sufficiently rounded, dull, detuned or blunt so as to allow the needle 10 to be used to aspirate the lens capsule 17 of an eye and not damage it with minimally sustained aspiration.

With the rounding of the outer and inner edges 15, 16 at the distal end tip 14 of the needle 10, the safety of the intraocular structures is greatly increased. Incidental contact of the distal end tip 14 to the capsule 17 or iris of a patient's eye will no longer result in damage to these structures, nor will these structures be damaged during surgical procedures involving minimally sustained aspiration. The rounded outer and inner edges 15, 16 can improve the safety to the capsule 17 of an eye, while still allowing the capsule 17 to come into contact with the distal end tip 14 of the needle.

The external diameter of the cylindrical outer surface 13 remains constant near the distal end 14 of the needle 10, and the external diameter of the distal end tip 14 does not exceed the external diameter of the cylindrical outer surface 13. In most of the embodiments disclosed herein, the external diameter of the cylindrical outer surface 13 near the distal end of the needle 10 does not exceed a standard outer diameter of a conventional 19- or 20-gauge phacoemulsification needle. By preserving the standard external diameter of the needle 10, this will facilitate manufacturing, allow for ease of transition for surgeons from the sharpened tips to the rounded tips of the present invention, and most of all, allow for continued use of the microincisions necessary for sleeveless bimanual phacoemulsification.

The needle 10 can be manufactured by first lathing a needle from a solid block of material to a uniform standard outer diameter. The needle 10 is then bored to form the lumen 18. Various other forms of metalworking can also be performed on the needle to change the configuration of the lumen or the outer surface dimensions of the needle. Once the lumen 18 is formed, the outer and inner edges 15, 16 are rounded to eliminate any sharp edges that would otherwise tend to cut tissue during use.

Figure 6:
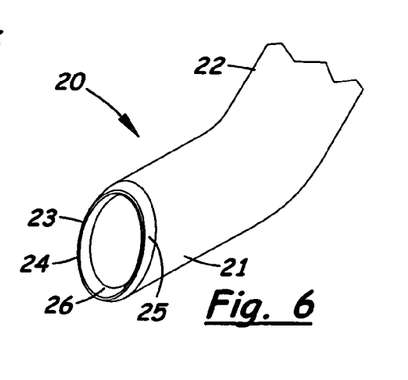
FIG. 6 is a perspective view of a needle having an angled tip configuration with rounded inner and outer edges according to another embodiment of the present invention.

A phacoemulsification needle 20 according to a second embodiment of the present invention is shown in FIG. 6. The needle 20 in this embodiment is the same as the needle 10 in the first embodiment, except that the distal portion 21 of the needle 20 is angled from the proximal portion 22, and the distal end tip 23 has a distal edge that slopes at an angle other than 90 degrees relative to a longitudinal axis of the distal portion 21 of the needle 20. The distal edge of the distal end tip 23 has rounded outer and inner edges 25, 26 to maintain the integrity of the capsule and other intraocular structures that might be damaged by a sharp edge.

With the change to a needle 10, 20 with a distal tip 14, 24 having rounded outer and inner edges, the risk of damage to the capsule from the aspirating opening of the needle becomes significantly diminished. While improving safety of the intraocular structures as described above, this improvement in the safety of the aspiration makes it possible to innovate new designs to improve the efficiency of phacoemulsification. Accordingly, several additional embodiments of phacoemulsification needles incorporating the teachings of the Applicant's invention will now be described.

Figure 9:
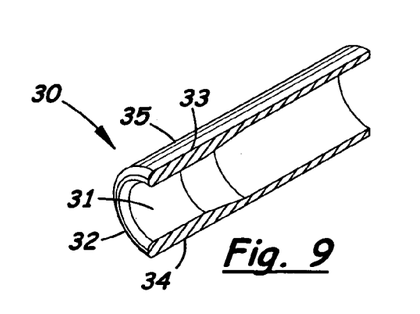
FIG. 9 is a cutaway perspective view of a phacoemulsification needle having a reduced inner diameter at a distal end portion according to another embodiment of the present invention.
Figure 10:
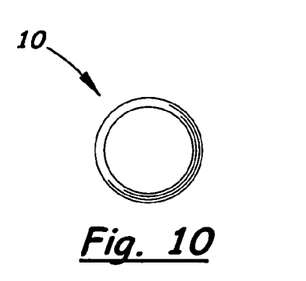
FIG. 10 is an end view of the phacoemulsification needle shown in FIG. 5 having a relatively thin sidewall thickness.
Figure 11:
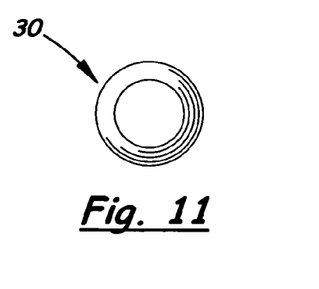
FIG. 11 is an end view of the phacoemulsification needle shown in FIG. 9 having a reduced inner diameter and a thickened sidewall.

A phacoemulsification needle 30 according to another embodiment of the present invention is shown in FIGS. 9 and 11. The needle 30 in this embodiment has a central opening 31 at the distal end tip 32, similar to the distal end tip 14 of the needle 10 shown in FIG. 1. However, the cylindrical sidewall 33 at the distal portion 34 of the needle 30 in this embodiment has an increased thickness, while the outer diameter of the cylindrical outer surface 35 remains constant over the distal portion 34 to preserve the normal external diameter of the needle 30. The increased thickness of the sidewall 33 at the distal portion 34 results in a narrowing of the central opening 31 at the distal end tip 32. The increased thickness of the sidewall 33 can be seen by comparing FIGS. 10 and 11, wherein FIG. 10 is an end view of the needle 10 shown in FIG. 1 in which the sidewall thickness remains constant, and FIG. 11 is an end view of the needle 30 shown in FIG. 9 in which the thickness of the sidewall 33 increases at the distal portion 34.

The increased thickness of the sidewall 33 in this embodiment extends a short distance along the distal portion 34 of the needle 30, approximately equal in length to the diameter of the central opening 31. The sidewall thickness rapidly thins on the proximal side of the thickened distal portion 34 until it reaches the original sidewall thickness and inner diameter of the needle 30. The distal end tip 32 is again rounded on its inner and outer edges, as in the embodiments described above. The thicker sidewall distal portion 34 of this embodiment will provide two additional benefits. The first is to increase the energy of the tip 32 by increasing the flat surface area at the tip for improving cavitation. The second is to diminish the size of the emulsified or fragmented material, allowing it to pass more easily through the remainder of the phacoemulsification needle 30 and tubing and improve the stability of the anterior chamber by diminishing the "bounce" or "surge" effect as pieces of nucleus or other fragmented material are passed through the tubing.

Figure 12:
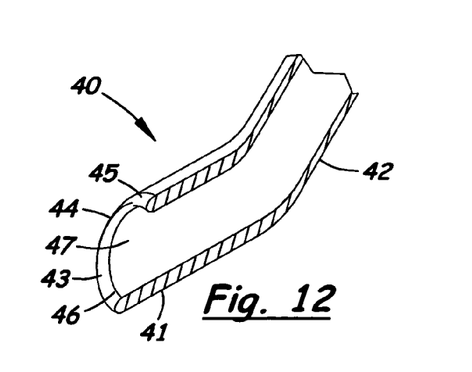
FIG. 12 is a cutaway perspective view of a phacoemulsification needle having an angled tip and a thickened sidewall at a distal end portion of the needle according to another embodiment of the present invention.

A phacoemulsification needle 40 according to another embodiment of the present invention is shown in FIG. 12. The needle 40 in this embodiment is the same as the needle 30 shown in FIG. 9, except that the distal portion 41 of the needle 40 is angled from the proximal portion 42, and the distal end tip 43 has a distal edge 44 that slopes at an angle other than 90 degrees relative to a longitudinal axis of the distal portion 41 of the needle 40. The distal edge 44 of the distal end tip 43 is rounded on the outer and inner edges 45, 46 to provide an operating tip without any sharp edges that might come into contact with an aspirated capsule. The needle 40 has an increased sidewall thickness at the distal portion 41 that results in a narrowing of the central opening 47 at the distal end tip 43 similar to the needle 30 shown in FIG. 9.

Figure 13:
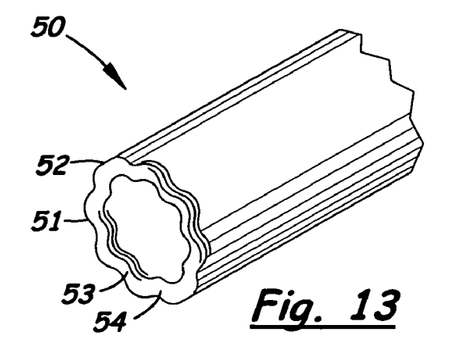
FIG. 13 is a perspective view of a phacoemulsification needle having a serrated distal end tip according to another embodiment of the present invention.
Figure 14:
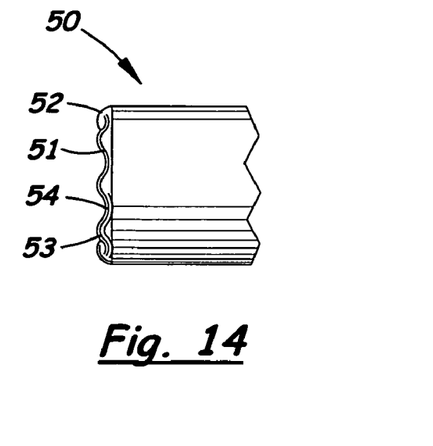
FIG. 14 is an end view of the phacoemulsification needle shown in FIG. 13.

A phacoemulsification needle 50 according to another embodiment of the present invention is shown in FIGS. 13 and 14. The needle 50 in this embodiment has a serrated edge 51 at the distal end tip 52. The serrations 53 and the gaps 54 between the serrations 53, as well as the inner and outer edges thereof, are rounded to eliminate any sharp cutting edges at the distal end tip 52. The serrations 53 can be provided in a variety of different patterns to fit a given application or operating technique. The number of serrations 53 can also be varied to suit a particular application or technique. The serrations 53 may enhance phacoemulsification in some cases by decreasing the repulsive effect of cavitation in the gaps 54 between the serrations 53.

Figure 15:
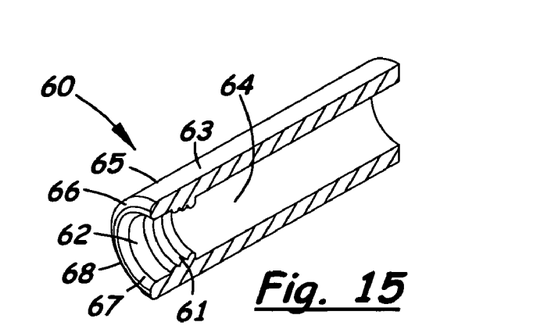
FIG. 15 is a cutaway perspective view of a phacoemulsification needle having concentric ridges on an inner surface of the needle according to another embodiment of the present invention.
Figure 16:
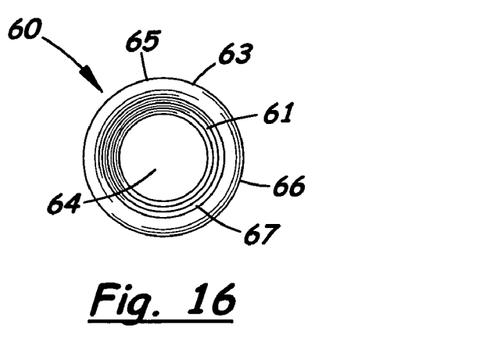
FIG. 16 is an end view of the phacoemulsification needle shown in FIG. 15.

A phacoemulsification needle 60 according to another embodiment of the present invention is shown in FIGS. 15 and 16. The needle 60 in this embodiment has a plurality of concentric ridges 61 or grooves on the inner surface 62 of the hollow member 63, which are concentric to a central lumen 64 of the hollow member 63. The concentric ridges 61 or grooves near the distal end portion 65 of the hollow member 63 are rounded, along with the outer and inner edges 66, 67 of the distal tip 68, to eliminate any sharp cutting edges at the distal end tip 68. Depending on the distance within the internal surface of the needle 60 that they extend, the concentric ridges 61 or grooves may regain their sharp configuration further into the lumen 64 of the needle 60 where they would be unlikely to contact the intraocular structures at risk for damage or otherwise affect the cutting process. With or without serrations, the concentric ridges 61 or grooves may enhance the effectiveness of the cavitation process during phacoemulsification. The number, size and/or pattern of concentric ridges 61 or grooves can be varied to suit a particular application or operating technique.

Figure 17:
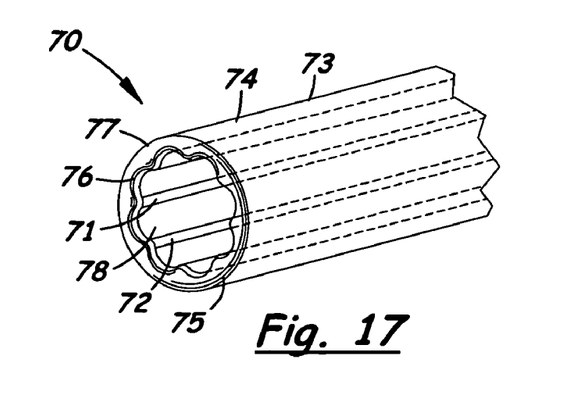
FIG. 17 is a perspective view of a phacoemulsification needle having longitudinal ridges on an inner surface of the needle according to another embodiment of the present invention.
Figure 18:
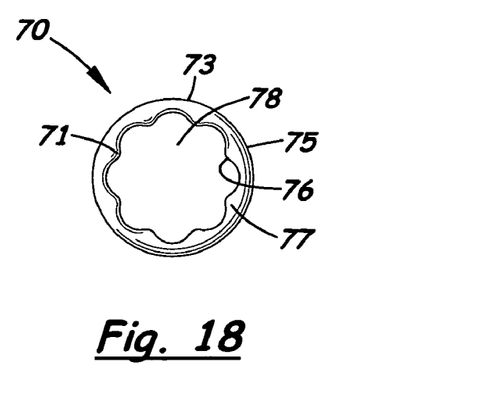
FIG. 18 is an end view of the phacoemulsification needle shown in FIG. 17.

A phacoemulsification needle 70 according to another embodiment of the present invention is shown in FIGS. 17 and 18. The needle 70 in this embodiment has a plurality of ridges 71 or grooves on the inner surface 72 of the hollow member 73, which extend longitudinally along the inner surface 72 of the hollow member 73. The longitudinal ridges 71 or grooves may extend all the way down the needle shaft, or only partway. The longitudinal ridges 71 or grooves near the distal end portion 74 of the hollow member 73 are rounded, along with the outer and inner edges 75, 76 of the distal tip 77, to eliminate any sharp cutting edges at the distal end tip 77. The longitudinal ridges 71 or grooves may regain their sharp configuration further into the lumen 78 of the needle 70 where they would be unlikely to contact the intraocular structures at risk for damage or otherwise affect the cutting process. With or without serrations, the longitudinal ridges 71 or grooves may enhance the effectiveness of the cavitation process during phacoemulsification. The number, size and/or pattern of longitudinal ridges 71 or grooves can be varied to suit a particular application or operating technique.

Figures 19, 20, 21, 22, 23, 24, 25, 26:
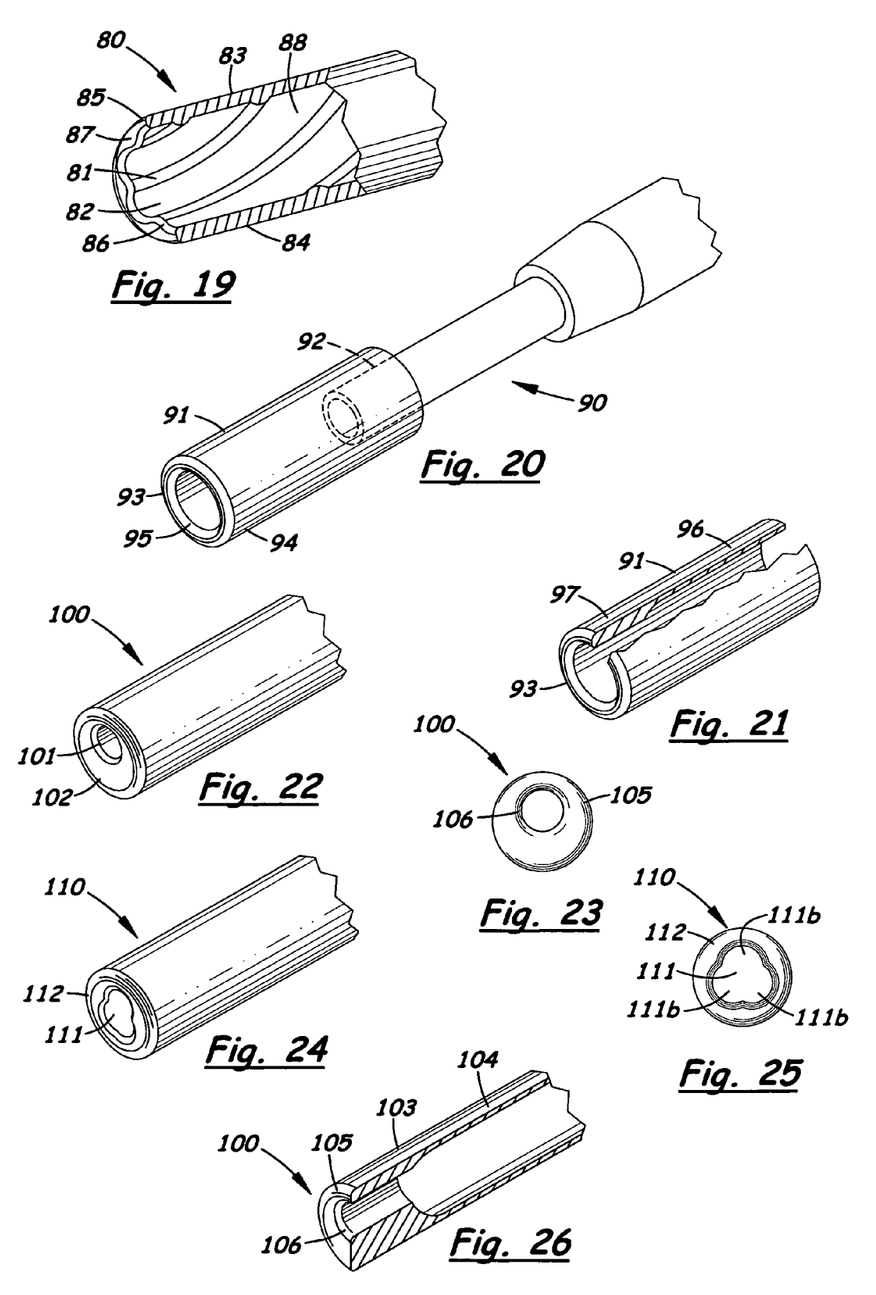
FIG. 19 is a cutaway perspective view of a phacoemulsification needle having ridges extending in a spiral configuration on an inner surface of the needle according to another embodiment of the present invention.
FIG. 20 shows a phacoemulsification needle having a sleeve positioned over the needle with rounded inner and outer edges at a distal end tip of the sleeve.
FIG. 21 shows a cutaway perspective view of the sleeve of the embodiment shown in FIG. 20.
FIG. 22 shows a perspective view of a phacoemulsification needle having an asymmetric bore according to another embodiment of the present invention.
FIG. 23 shows an end view of the needle shown in FIG. 22.
FIG. 24 shows a perspective view of a phacoemulsification needle having a plurality of asymmetric bores according to another embodiment of the present invention.
FIG. 25 shows an end view of the needle shown in FIG. 24.
FIG. 26 shows a cutaway perspective view of a phacoemulsification needle having an asymmetric bore that extends only partway through the needle according to another embodiment of the present invention.
Figure 27:
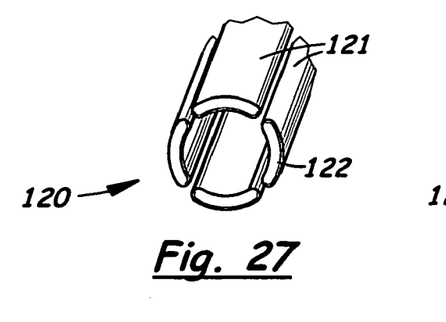
FIG. 27 shows a perspective view of a phacoemulsification device having an end portion formed by a plurality of rib segments according to another embodiment of the present invention.
Figure 28:
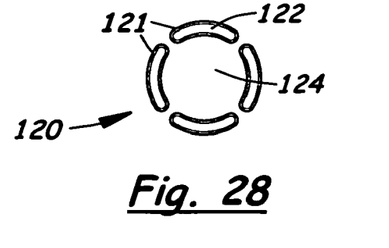
FIG. 28 is an end view of the device shown in FIG. 27.

A phacoemulsification needle 80 according to another embodiment of the present invention is shown in FIG. 19. The needle 80 in this embodiment has a plurality of ridges 81 or grooves on the inner surface 82 of the hollow member 83, which extend in a spiral configuration similar to "rifling" along the inner surface 82 of the hollow member 83. The spiral ridges 81 or grooves near the distal end portion 84 of the hollow member 83 are rounded, along with the outer and inner edges 85, 86 of the distal tip 87, to eliminate any sharp cutting edges at the distal end tip 87. The spiral ridges 81 or grooves may regain their sharp configuration further into the lumen 88 of the needle 80 where they would be unlikely to contact the intraocular structures at risk for damage or otherwise affect the cutting process. With or without serrations, the spiral ridges 81 or grooves may enhance the effectiveness of the cavitation process during phacoemulsification. The number, size and/or pattern of spiral ridges 81 or grooves can be varied to suit a particular application or operating technique.

A phacoemulsification needle assembly 90 according to another embodiment of the present invention is shown in FIG. 20. The needle assembly 90 in this embodiment has a removable sleeve 91 that has the capacity of transmitting some ultrasound energy. The removable sleeve 91 slides over the regular metal needle tip 92 and prevents the full transmission of power from the metal needle tip 92 underneath. The removable sleeve 91 may be useful for beginning a case to determine whether the lens/cataract could be removed with vacuum power alone. The sleeve 91 could then be removed if the lens required the transmission of ultrasonic power. Irrigation may or may not be intrinsic to the needle assembly 90 having a removable sleeve 91 according to this embodiment. The distal tip 93 of the removable sleeve 91 will preferably have rounded outer and inner edges 94, 95 to eliminate any sharp cutting edges at the distal tip 93. The sleeve 91 can also be made of a soft material, such as a plastic composite or rubber material. The sleeve 91 according to this embodiment can be used with a conventional phacoemulsification needle 92 having sharp edges at the tip (which are covered by the sleeve during use), or the sleeve 91 can be used with the various phacoemulsification needles with rounded edges according to the other embodiments of the present invention described herein.

As shown in FIG. 21, the removable sleeve 91 of the phacoemulsification needle assembly 90 can have a relatively thin wall dimension along the portion 96 of the sleeve 91 that covers the needle 92, and a thicker wall dimension at the distal portion 97 of the sleeve 91. This configuration allows the sleeve 91 to correspond more closely to the typical inner and outer dimensions of the phacoemulsification needles used by surgeons, and allows the surgeon to keep the incision size at a minimum. The distal portion 97 of the sleeve 91 could also have a reduced outer dimension to match the typical outer dimension of the phacoemulsification needle 92 on which it is used.

A phacoemulsification needle 100 according to another embodiment of the present invention is shown in FIGS. 22, 23 and 26. The needle 100 in this embodiment has a lumen 101 which is asymmetrically placed to increase the thickness or thinness of a specific region of the distal tip 102 of the needle. The asymmetric placement of the lumen 101 functions to increase or decrease the relative effectiveness of ultrasonic energy emanating from the tip 102 during a phacoemulsification procedure. As shown in FIG. 26, the asymmetric portion of the lumen 101 may be limited to the distal portion 103 of the needle 100, with the proximal portion 104 of the lumen 101 being larger and centrally located. The needle 100 with an asymmetric lumen according to this embodiment will preferably have rounded outer and inner edges 105, 106 at the distal tip 102 to eliminate any sharp cutting edges at the distal tip 102. However, a phacoemulsification needle having an asymmetric lumen with conventional sharp cutting edges may also be suitable for some applications and surgical techniques.

A phacoemulsification needle 110 according to another embodiment of the present invention is shown in FIGS. 24 and 25. The needle 110 in this embodiment has a lumen 111 which is created by multiple asymmetrical borings 111b of the same needle 110. The multiple borings 111b will create an unusual outer edge configuration, which may function to increase or decrease the relative effectiveness of ultrasonic energy emanating from the tip 112 during a particular phacoemulsification procedure.

A phacoemulsification needle 120 according to another embodiment of the present invention is shown in FIGS. 27 to 31. The needle 120 in this embodiment has a plurality of distinct ribs 121, each of which can be partial segments of a cylinder so that when assembled and used together the ribs 121 form a generally cylindrical shape (e.g., similar to barrel staves). The ribs 121 can transmit ultrasonic forces independently of each other for the purpose of removing material in close proximity to their distal tips 122. This independent transmission may be synchronous to mimic the current needle energy delivery, or asynchronous, or dyssyncronous. These variations in energy delivery will allow for greater accuracy in the delivery of ultrasonic energy.

Figure 29:
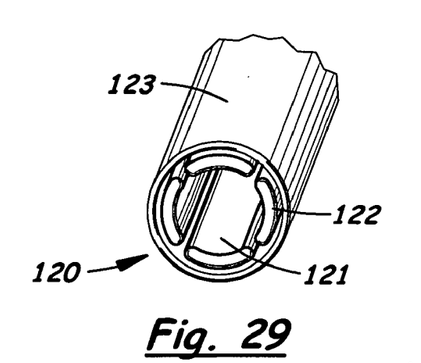
FIG. 29 shows the phacoemulsification device of FIG. 27 with a sleeve positioned over the plurality of rib segments.
Figure 30:
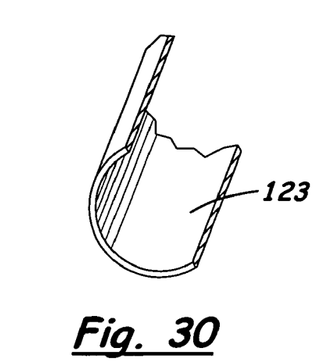
FIG. 30 shows a cutaway perspective view of the sleeve of the phacoemulsification device of FIG. 29.
Figure 39:
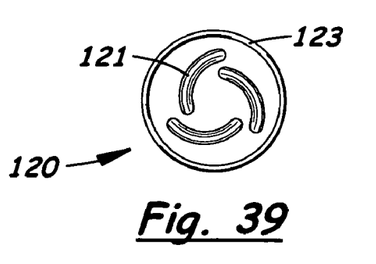
FIG. 39 is an end view of a phacoemulsification device having a plurality of rib segments collapsed within a sleeve in an unassembled condition.
Figure 40:
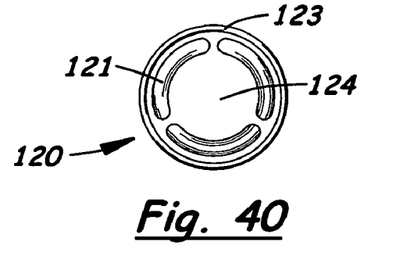
FIG. 40 is an end view of a phacoemulsification device having a plurality of rib segments arranged within a sleeve in an assembled condition.

The ribs 121 are supported by an outer sleeve 123 of inert material, as shown in FIGS. 29 and 30. The sleeve 123 may be flexible, making it possible to collapse the ribs 121 together, as shown in FIG. 39, to form a smaller diameter instrument for insertion through a smaller diameter incision. Once the distal tip 122 is inside the eye, the ribs 121 may be repositioned into a cylindrical configuration, as shown in FIGS. 29 and 40, to form a normal internal lumen diameter for performing phacoemulsification.

Figure 41:
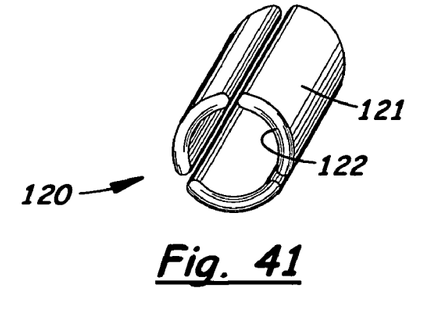
FIG. 41 is a perspective view of a phacoemulsification device having a plurality of rib segments.
Figure 42:
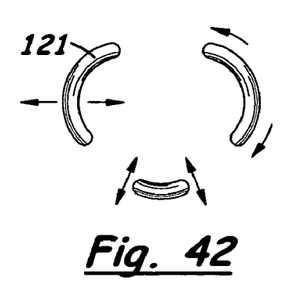
FIG. 42 is an exploded end view of the rib segments shown in FIG. 41 showing directions of possible vibrating movement for the rib segments.

Each of the ribs 121 are capable of movement in a variety of directions, as shown in FIGS. 41 and 42, other than the traditional piston-like movement of a standard phacoemulsification needle. For example, the ribs 121 can be made in such a way to be able to pivot on any axis (e.g., as a child's see-saw pivots on its central support). The ribs 121 can also be made to have a vertical or horizontal movement as viewed end-on from their distal tips 122. The pivoting action and vertical or horizontal movement can be synchronous, asynchronous or dyssynchronous.

Because the ribs 121 will allow different options for modifying the lumen 124 of the needle, the ribs 121 can be made of a variety of materials, including some materials that are rather exotic to ophthalmology at present. For example, the ribs 121 can be made of ceramic or carbon fiber composites, polymers, or standard titanium. The power transmitted down the individual rib 121 will be less than that of a standard needle, thereby making different demands on the components and materials to resist the forces of transmitting ultrasound.

Figures 31, 32, 33:
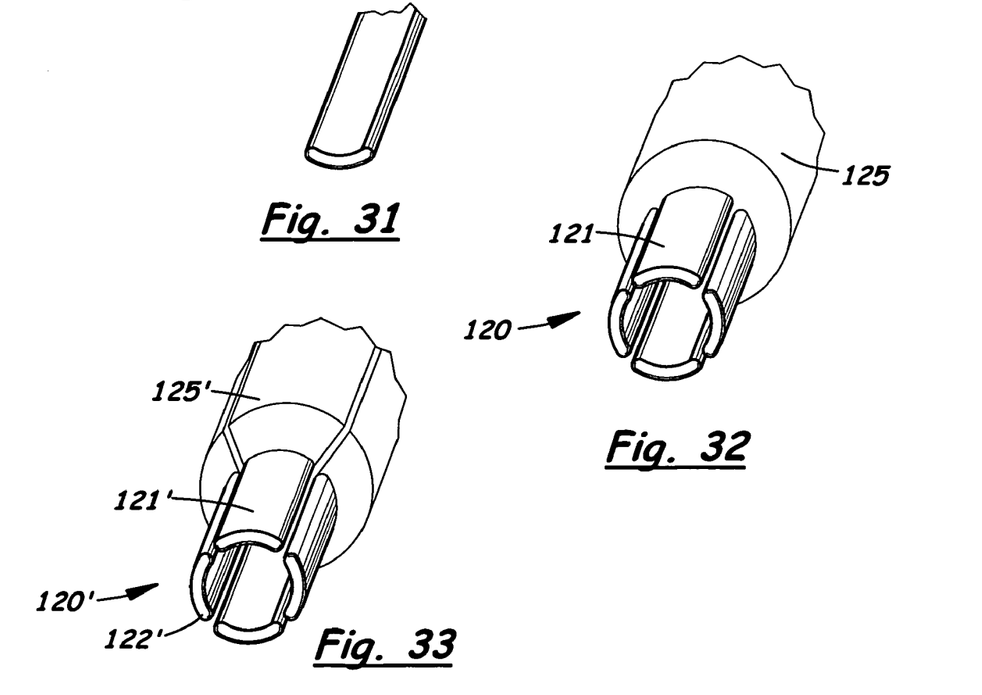
FIG. 31 shows a perspective view of one of the rib segments of the phacoemulsification needle of FIG. 27.
FIG. 32 shows a phacoemulsification device having a plurality of rib segments joined together at a hub.
FIG. 33 shows a phacoemulsification device having a plurality of rib segments separated at a hub.

The ribs 121 can be served by a single transducer or set of transducers that drives a common hub 125 or the like on which the ribs are attached, as shown in FIG. 32. Alternatively, the individual ribs 121' can remain separate at the hub 125', as shown in FIG. 33, so that the ribs 121' can be driven by a plurality of individual transducers or sets of transducers carried by the handpiece. The individual transducers or sets of transducers can be used to drive the individual ribs 121' independently to deliver ultrasonic energy with greater accuracy and in a desired fashion to the distal tip 122' of the instrument.

Figure 34:
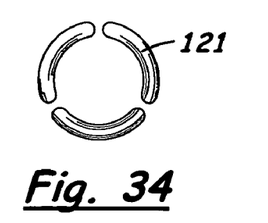
FIG. 34 is an end view of a phacoemulsification device having a plurality of symmetrically arranged rib segments.
Figure 35:
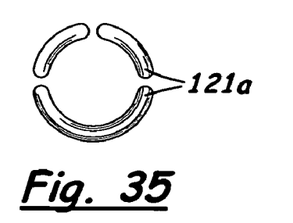
FIG. 35 is an end view of a phacoemulsification device having a plurality of asymmetrically arranged rib segments.
Figure 36:
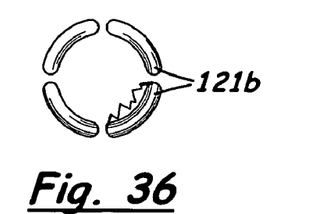
FIG. 36 is an end view of a phacoemulsification device having a plurality of different rib segments.
Figure 37:
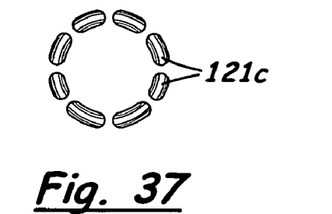
FIG. 37 is an end view of another phacoemulsification device having a plurality of different rib segments.
Figure 38:
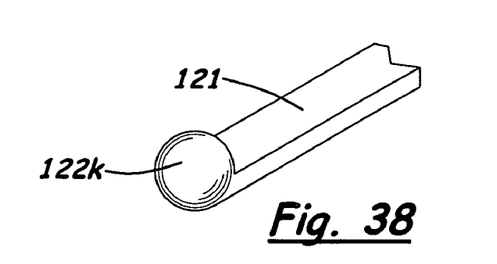
FIG. 38 shows a rib segment for a phacoemulsification device having a knobbed end.

The ribs 121 can be formed and arranged in a variety of ways to best suit a particular operating procedure or technique. For example, a plurality of ribs 121 can be formed and arranged in a symmetric manner as shown in FIG. 34; a plurality of ribs 121a can be formed and arranged in an asymmetric manner as shown in FIG. 35; a plurality of ribs 121b can be formed and arranged in a variable asymmetric manner as shown in FIG. 36; or a plurality of ribs 121c can be formed and arranged in a further variable asymmetric manner as shown in FIG. 37. Moreover, each rib 121 can have a straight configuration at its distal tip 122, as shown in FIG. 31, or a knobbed configuration 122k at its distal tip, as shown in FIG. 38. The distal tips 122 of the ribs 121 will preferably have rounded inner, outer and side edges to eliminate any sharp cutting edges near the distal tip of the instrument.

Figure 43:
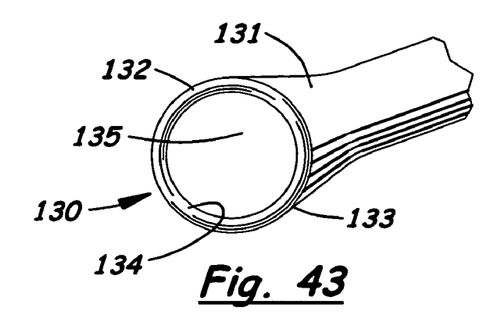
FIG. 43 is a perspective view of a phacoemulsification needle having a flared end portion with a substantially constant sidewall thickness and rounded inner and outer edges.
Figure 44:
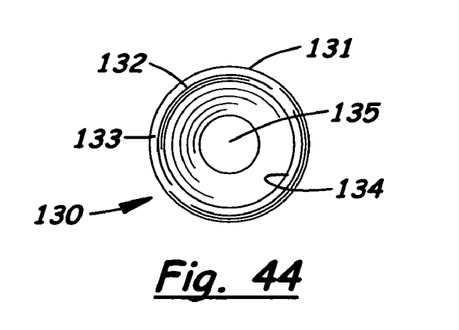
FIG. 44 is an end view of the phacoemulsification needle shown in FIG. 43.

Variations of the above embodiments can also be made. For example, a phacoemulsification needle 130 having a flared distal end portion 131 can be provided, as shown in FIGS. 43 and 44. The flared distal end portion 131 in this embodiment has a substantially constant sidewall thickness so that the inner diameter of the needle increases at approximately the same rate as the outer diameter toward the distal end tip 132. The outer and inner edges 133, 134 at the distal end tip 132 of the needle 130 are rounded to eliminate any sharp cutting edges at the distal end tip 132, as in the embodiments described above. This embodiment is similar to a so-called "cobra" tip needle known in the art, except that the sharp cutting edges are eliminated to thereby avoid damaging the capsule and other intraocular structures that can be aspirated into the lumen 135 during phacoemulsification procedures.

Figure 45:
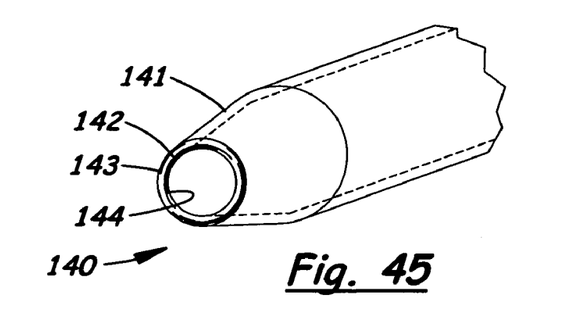
FIG. 45 is a perspective view of a phacoemulsification needle having a reduced diameter end portion with a substantially constant sidewall thickness and rounded inner and outer edges.

For another example, a phacoemulsification needle 140 having a reduced diameter distal end portion 141 can be provided, as shown in FIG. 45. The reduced diameter distal end portion 141 in this embodiment has a substantially constant sidewall thickness so that the inner diameter of the needle 140 decreases at approximately the same rate as the outer diameter toward the distal end tip 142. The outer and inner edges 143, 144 at the distal end tip 142 of the needle 140 are rounded to eliminate any sharp cutting edges at the distal tip 142, as in the embodiments described above.

Another example variation is that the needles described herein can be modified to have an angled distal portion and/or a distal edge that slopes at an angle other than 90 degrees relative to the longitudinal axis of the needle. For another example variation, the needle 50 shown in FIGS. 13 and 14 can be modified by making the serrations thickened, with both or either concentric and radial grooves or ridges at the distal tip of the needle in such a way as to enhance removal of nuclear material.

The phacoemulsification needles described herein can be made of a variety of different materials without departing from the scope of the present invention. For example, titanium alloys, stainless steel alloys, and various other materials capable of transmitting ultrasound energy for the purpose of phacoemulsification can be used for the needles.

A number of different processes can be used to round the edges of the phacoemulsification needles of the present invention. For example, the edges at the distal end tips of the needles can be rounded by filing, molding, machining, or other processes known in the art.

The rounded surfaces of the phacoemulsification needles of the present invention may be rounded, dulled, detuned or blunted to create surfaces that lack any sharp edges so that the needles can be used to aspirate the lens capsule and not damage it with minimally sustained aspiration. The rounded surfaces are preferably hardened to resist nicking, burring and scuffing. These causes of damage might otherwise tend to undo the benefit of practicing phacoemulsification without using sharp cutting surfaces. The needles can be hardened by applying hard surface coatings, annealing, or using other conventional hardening techniques.

While the invention has been specifically described in connection with specific embodiments thereof, it is to be understood that this is by way of illustration and not of limitation, and the scope of the appended claims should be construed as broadly as the prior art will permit.

What is claimed is:

1. A phacoemulsification needle, comprising:
a hollow member having an inner surface defining a lumen, an outer surface, and a distal end tip;
wherein an outer diameter of the distal end tip does not exceed an outer diameter of the outer surface of the hollow member adjacent to the distal end tip; and
wherein said distal end tip has an outer edge portion and an inner edge portion, and wherein said outer and inner edge portions are rounded to eliminate any sharp edges, said rounded inner edge portion providing a smooth, rounded transition between said distal end tip and said lumen to maintain the integrity of intraocular structures that are aspirated into the lumen during a surgical procedure.

2. The needle according to claim 1, wherein said outer surface is substantially cylindrical with a uniform outer diameter near the distal tip of the needle.

3. The needle according to claim 1, wherein said outer and inner edge portions are rounded to form a fully rounded distal end tip with a continuous curvature from the outer surface to the inner surface of the hollow member.

4. The needle according to claim 1, wherein said outer and inner edge portions are rounded to form a distal tip with a blunt surface between the outer and inner edge portions.

5. The needle according to claim 1, wherein a thickness of a sidewall of said hollow member increases at a distal portion of the hollow member so that the thickness is greatest immediately adjacent to the distal end tip, while an outer diameter of the outer surface remain constant over said distal portion.

6. The needle according to claim 1, wherein a distal portion of the hollow member is bent at an angle relative to a proximal portion of the hollow member, and the distal end tip is defined by a distal edge that slopes at an angle other than 90 degrees relative to a longitudinal axis of the distal portion of the hollow member.

7. The needle according to claim 1, wherein said distal end tip of the needle is serrated.

8. The needle according to claim 1, wherein said inner surface of the hollow member has a plurality of ridges or grooves.

9. The needle according to claim 8, wherein said ridges or grooves are concentric to an opening of the hollow member.

10. The needle according to claim 8, wherein said ridges or grooves extend longitudinally along the inner surface of the hollow member.

11. The needle according to claim 8, wherein said ridges or grooves extend in a spiral configuration along the inner surface of the hollow member.

12. The needle according to claim 8, wherein at least a portion of said ridges or grooves near a distal end portion of the hollow member have rounded surfaces.

13. The needle according to claim 1, wherein said hollow member is a removable sleeve positioned over a distal end portion of an ultrasonically driven structure, said removable sleeve having outer and inner edges at its distal end tip that are rounded to eliminate any sharp edges.

14. The needle according to claim 13, wherein said removable sleeve has a proximal portion positioned over the ultrasonically driven structure and a distal portion that extends past said ultrasonically driven structure, and wherein said proximal portion of the removable sleeve has a thinner sidewall than said distal portion thereof.

15. The needle according to claim 1, wherein said hollow member has an asymmetric lumen extending through a distal portion thereof, and said rounded inner edge portion provides a smooth transition between a distal end tip of the hollow member and said asymmetric lumen.

16. The needle according to claim 15, wherein said asymmetric lumen comprises a plurality of asymmetric bores extending through a distal portion of said hollow member.

17. The needle according to claim 1, wherein a distal portion of said hollow member has a reduced outer diameter in a direction toward said distal end tip, and wherein a sidewall thickness of said hollow member remains substantially constant over said distal portion.

18. A method of performing phacoemulsification, comprising the steps of:
   providing a phacoemulsification needle comprising a hollow member having an inner surface defining a lumen, an outer surface, and a distal end tip having an outer diameter that does not exceed an outer diameter of the outer surface of the hollow member adjacent to the distal end tip, said distal end tip having outer and inner edge portion which are rounded to eliminate any sharp edges, said rounded inner edge portion providing a smooth, rounded transition between said distal end tip and said lumen to maintain the integrity of intraocular structures that are aspirated into the lumen during a surgical procedure; and
   using the phacoemulsification needle to deliver ultrasonic energy to emulsify unwanted tissue at a surgical site and to aspirate the unwanted tissue through the hollow member without using a sharp surface to cut the unwanted tissue.

19. The method according to claim 18, wherein said outer surface of the hollow member is substantially cylindrical with a uniform outer diameter near the distal end tip of the needle.

20. A phacoemulsification instrument, comprising:
   a source of ultrasonic energy;
   a plurality of ribs arranged in a pattern and extending from said source of ultrasonic energy, whereby said ribs can be used to transmit ultrasonic forces independent of each other for removing material in close proximity to respective distal tips of the ribs; and
   an outer sleeve separate from said plurality of ribs positioned over and supporting said plurality of ribs;
   wherein said plurality of ribs are each driven independently by individual transducers.

21. The method according to claim 20, wherein the distal tips of said ribs are rounded to eliminate any sharp edges.

22. A phacoemulsification needle, comprising:
   a hollow member having an inner surface defining a lumen, an outer surface, and a distal end tip;
   wherein said distal end tip comprises an initial cutting surface that defines an outermost extent of said distal end tip and does not exceed an outer diameter of the outer surface of the hollow member adjacent to the distal end tip; and
   wherein said distal end tip has an outer edge portion and an inner edge portion, and wherein said outer and inner edge portions are rounded to eliminate any sharp edges, said rounded inner edge portion providing a smooth, rounded transition between said distal end tip and said lumen to maintain the integrity of intraocular structures that are aspirated into the lumen during a surgical procedure.

23. A phacoemulsification needle, comprising:
   a hollow member having an inner surface defining a lumen, an outer surface, and a distal end tip;
   wherein said outer surface is substantially cylindrical, and an outer diameter of the distal end tip does not exceed an outer diameter of the cylindrical outer surface adjacent to the distal end tip; and
   wherein said distal end tip has an outer edge portion and an inner edge portion, and wherein said outer and inner edge portions are rounded to eliminate any sharp edges, said rounded inner edge portion providing a smooth, rounded transition between said distal end tip and said lumen to maintain the integrity of intraocular structures that are aspirated into the lumen during a surgical procedure.

24. A phacoemulsification needle, comprising:
   a hollow member having an inner surface defining a lumen, an outer surface, and a distal end tip;
   wherein a distal portion of said hollow member is flared such that an outer diameter of the outer surface increases in a direction toward said distal end tip, and said outer surface is free of any bulbous structure protruding outwardly from the hollow member adjacent to the distal end tip; and
   wherein said distal end tip has an outer edge portion and an inner edge portion, and wherein said outer and inner edge portions are rounded to eliminate any sharp edges, said rounded inner edge portion providing a smooth, rounded transition between said distal end tip and said lumen to maintain the integrity of intraocular structures that are aspirated into the lumen during a surgical procedure.

* * * * *